United States Patent [19]

Kroll

[11] Patent Number: 4,672,976
[45] Date of Patent: Jun. 16, 1987

[54] HEART SOUND SENSOR

[75] Inventor: Mark W. Kroll, Rogers, Minn.

[73] Assignee: Cherne Industries, Inc., Minneapolis, Minn.

[21] Appl. No.: 872,514

[22] Filed: Jun. 10, 1986

[51] Int. Cl.$^4$ ............................................. A61B 7/02
[52] U.S. Cl. .................................. 128/715; 128/773; 381/169; 381/187
[58] Field of Search ............... 128/715, 773, 660, 639, 128/644, 802–803; 381/153–154, 169–169, 187–188

[56] References Cited

U.S. PATENT DOCUMENTS

| | | | |
|---|---|---|---|
| 1,282,908 | 10/1918 | Miller | 128/715 X |
| 2,518,331 | 8/1950 | Kalin | 128/715 X |
| 2,614,144 | 10/1952 | Howatt | 128/715 X |
| 2,702,354 | 2/1955 | Chorpening | 128/715 X |
| 3,387,149 | 6/1968 | Young | 128/715 X |
| 3,525,810 | 8/1970 | Adler | 179/1 |
| 3,573,394 | 4/1971 | Birnbaum | 128/715 |
| 3,971,962 | 7/1976 | Green | 128/660 X |
| 4,154,231 | 5/1979 | Russell | 128/663 |
| 4,170,717 | 10/1979 | Walshe | 179/1 |
| 4,216,766 | 8/1980 | Duykers | 128/773 |
| 4,220,160 | 9/1980 | Kimball | 128/715 |
| 4,409,986 | 10/1983 | Apple et al. | 128/715 |
| 4,458,687 | 7/1984 | Dickson | 128/715 X |
| 4,483,343 | 11/1984 | Beyer et al. | 128/660 |
| 4,559,953 | 12/1985 | Wright et al. | 128/715 X |

OTHER PUBLICATIONS

Bacon; "Characteristics of a PVDF Membrane Hydrophone"; *IEEE Trans. on Sonics and Ultrasonics*, vol. SV-29; No. 1; 1-1982, pp. 18–25.

Primary Examiner—Lee S. Cohen
Assistant Examiner—Angela D. Sykes
Attorney, Agent, or Firm—Anthony G. Eggink

[57] ABSTRACT

A heart sound sensing device for placement on the body of a patient and for the detection of low frequency sound waves. The device is for use with medical diagnostic devices, and comprises a cylindrical housing structure for retaining the remaining elements of the device, a strap for holding the device to the body of the patient, a fluid ingress/egress aperture, an open end for receiving sound waves, and a hydrophone assembly centrally fixed within the housing structure for producing electrical signals in response to transmitted heart sound waves. The device of this invention is further provided with a flexible diaphragm which is vibratingly sensitive to sound waves generated by the patient's heart and being for placement in direct contact with the patient body surface to conform to the body contours. A bubble free fluid medium is provided to fill the remaining interior volume of the housing structure to transmit sound waves from the diaphragm to the hydrophone assembly. The device further includes a cable means communicatively connected to the hydrophone assembly for transmitting electrical output signals to medical diagnostic devices. The sound sensing device is further used in a method for sensing heart sound waves.

16 Claims, 6 Drawing Figures

HEART SOUND SENSOR

BACKGROUND OF THE INVENTION

This invention relates to medical diagnostic devices and, more particularly, to medical sensing devices used to detect energy in the audible range. This invention is particularly useful for the detection of a broad range of frequencies of bioacoustic waves generated by the human heart.

In the past, a variety of devices have been utilized to detect heart sounds. These devices range from primarily mechanical devices, such as the stethoscope, to various electronic devices, such as microphones and transducers. These prior art devices have various limitations including the inability to simultaneously detect high and low frequencies, the requirement of continuous "hands-on" operator manipulation, and sound wave distortion and attenuation.

Despite the need for a bio-acoustic sensing device in the medical diagnostic art which provides for the reliable transmission of sound waves, particularly in the sub-kilohertz (KHz) range, and which overcomes these prior art limitations, none insofar as is known has been proposed or developed.

Accordingly, it is an object of the present invention to provide a device that is easy to operate, that detects a broad range of heart sound frequencies, particularly low frequency sounds, and that minimizes heart sound wave distortion and attenuation.

SUMMARY OF THE INVENTION

The heart sound sensing device is for placement on the body of a patient to detect bio-acoustic signals. The device is for use with medical diagnostic devices, and comprises a cylindrical housing structure for retaining the remaining elements of the device, a securement belt assembly for holding the device to the body of the patient, a fluid ingress/egress aperture, an open end for receiving sound waves, and a hydrophone assembly centrally fixed within the housing structure for producing electrical signals in response to transmitted heart sound waves.

The housing structure is further provided with a flexible diaphragm disposed across its open end for placement in direct contact with the patient body surface and an interior having a bubble free fluid medium which permits sound wave transmission from the diaphragm to the hydrophone assembly.

The device of this invention further includes a cable means communicatively connected to the hydrophone assembly within the housing structure for transmitting electrical signals to medical diagnostic devices.

The device is generally thin and flat so that it will easily remain in a predetermined location on the precordial region of a patient. The securement belt assembly provided further enables one or a plurality of devices to be affixed in an operative position on the axillary region of the patient or to any body surface when the patient is either in a horizontal or non-horizontal position. Many prior art devices require continuous operator manipulation when in use because of their design features.

The device has a configuration which includes a hydrophone assembly which easily permits the detection of low frequency sound signals, particularly in the sub-KHz range, because of its sound wave reception aperture size. Prior art devices have been limited in their capacity to detect low sound frequencies, and, although hydrophones have been used in the acoustic art for specific applications, they have not been used in heart sound sensing devices of this nature.

The flexible membrane or diaphragm of the sound sensor device easily conforms to the contours of the patient body surface. This structural configuration and cooperation of elements enhances heart sound signal transfer and resolution by minimizing body surface and device gaps. Further, the flexible device structure minimizes sound wave loss and distortion by minimizing acoustical parameter differences between the materials used in its construction and patient body tissues.

A hydrophonic gel material, or a bubble-free liquid media, is provided to fill the interior of the housing structure and which serves to accurately transmit sound waves from the diaphragm to the immersed hydrophone assembly. Because prior art sound sensors generally utilize water as an acoustic transmission medium, the suspended gas bubbles contained therein can result in high sound wave attenuation or energy loss. These losses are primarily due to viscous forces as well as heat conduction losses associated with the compression and expansion of small gas bubbles by the passing sound wave.

Sound wave scattering is a further detrimental effect caused by gas bubbles in a transmission medium, and which results in the loss of energy in the sound wave. The presence of gas bubbles also affects the nature of the medium through which the wave progresses by altering its density and compressibility to, thereby, change the sound wave speed. Such medium alterations can result in a considerable amount of acoustic energy reflection and refraction losses. The device of the present invention is constructed to overcome the problems associated with the use of a water medium in sound sensor designs as well as the other prior art limitations previously described.

These and other benefits of this invention will become clear from the following description, by reference to the drawings.

DESCRIPTION OF THE PREFERRED EMBODIMENTS

Figure 1:
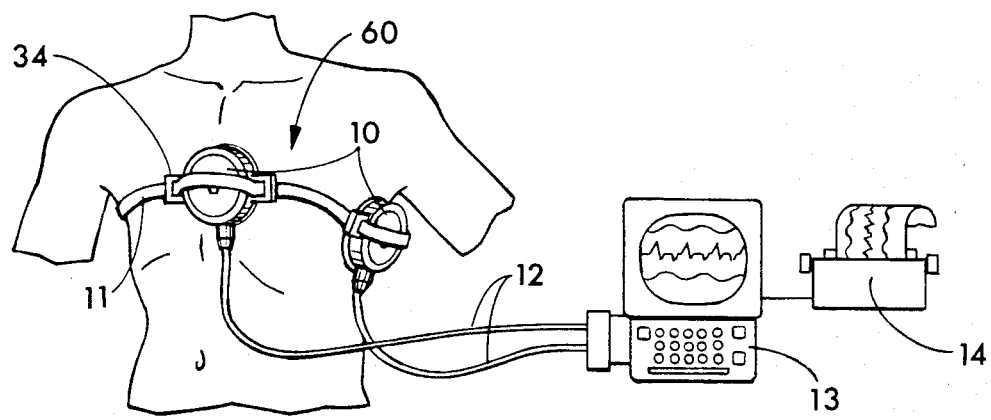
FIG. 1 shows a pair of heart sound sensor devices of the present invention placed in an operative position on the chest area of a patient.

FIG. 1 shows a pair of sound sensing devices 10 in an operative position at predetermined locations on the precordial region 60 of a patient. In use, prior to such placement, an acoustic coupling compound, such as Aquasonic 100 (T.M.), produced by Parker Labs, or Lectro-Sonic (T.M.), produced by Burdick, is applied to those predetermined locatins. A physician or other medical personnel determines the appropriate positioning locations on the precordial region for each device 10 depending upon the patient and upon the nature of the diagnostic test to be performed. The devices 10 are shown held in place by a strap means 11 which loops through securement means 34 of devices 10. The strap 11 is generally a flexible strap or band having end connectors or like fastening means to adjustably secure the devices 10 to the body of the patient.

The sound sensing device 10 is used to receive bioacoustic signals from the body of a patient. As shown in FIG. 1, the sound sensing devices 10 are arranged to receive transmitted sound waves from the heart of a patient and to convert the sound waves into electrical signals for use. The device 10, or a plurality of such devices 10 as shown, are used in conjunction with a medical diagnostic device 13 which processes electrical signals. The device 10 is communicatively connectable to the medical diagnostic device 13 via a cable or cable set 12. Subsequent to connection of the device or devices 10 to the medical diagnostic device 13, a sound sensing and analysis procedure is conducted. Additionally, as is shown in FIG. 1, the device 13 may be communicatively linked to a printer 14 for printed copy of diagnostic results.

Figure 2:
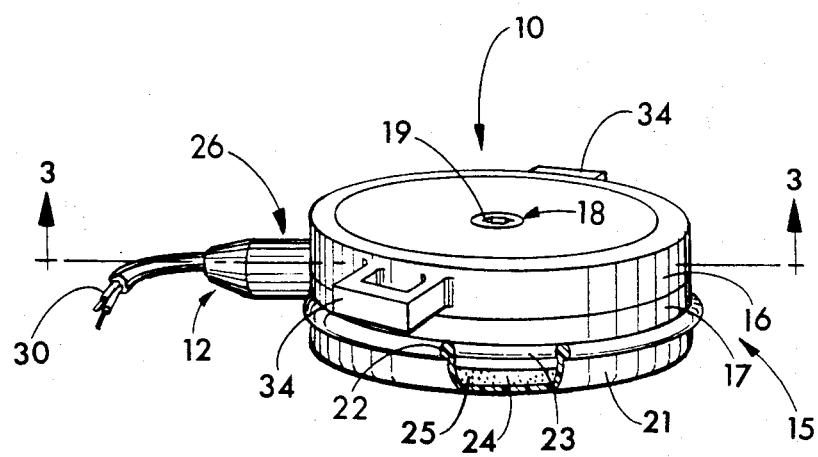
FIG. 2 is a view in perspective of the present invention and showing the device partially in cross-section for clarity.
Figure 3:
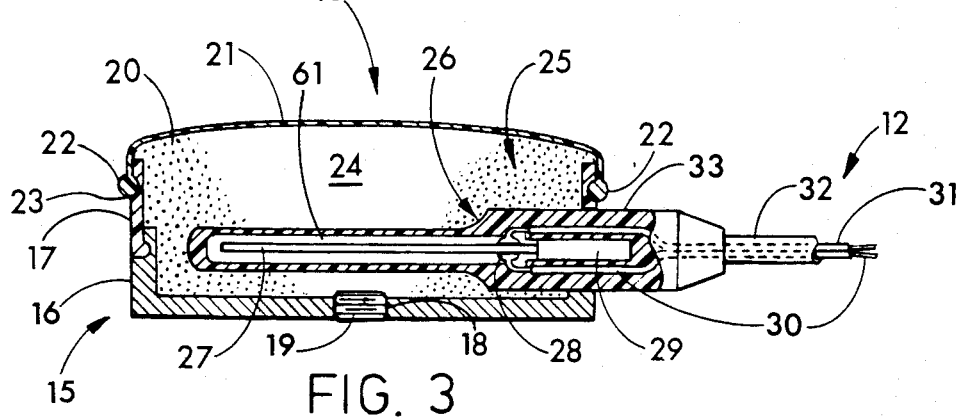
FIG. 3 is a cross-sectional view taken along lines 3—3 of FIG. 2 and which shows the interior of the sound sensor device housing structure.

FIGS. 2 and 3 show the sound sensing device 10 being comprised of a housing structure 15, a hydrophone assembly 26, a diaphragm 21, a hydrophonic gel medium 25 and a cable 12. The housing structure 15 is preferably cylindrical with one closed end and having a rigid portion 16, a pliant or semi-rigid portion 17, securement means 34, a fluid ingress/egress aperture 18, and a sound wave reception aperture 20. The housing structure 15 retains the operative elements of device 10 and also provides a chamber to receive transmitted sound waves. Securement means 34 of housing structure 15 serves to adjustably hold the strap or securement belt 11 to the device 10. The securement belt 11 is also able to adjustably hold a second sound sensing device 10, as shown in FIG. 1, and it also is provided with fastening means, such as a buckle or Velcro-fastening system to permit the adjustable securement of devices 10 about the chest of a patient.

The open bottom end or sound wave reception aperture 20 of housing structure 15 allows ingress of the transmitted sound waves. The sound wave reception aperture 20 is preferably 5 cm in diameter in one embodiment of the invention to allow for ingress of wavelengths on the order of magnitude of 10 cm. In this embodiment, the sound wave reception aperture 20 consists of the entire open end of the cylindrical housing structure 15 for the detection of low frequency sound waves.

The housing structure 15 shown has two-part body design; however, other housing structure configurations are also within the purview of this invention. The pliant or semi-rigid portion 17 of the housing structure 15 is flexible and comprised of a deformable and elastomeric material, for example, It, therefore, conforms to the contours of the body surface of the individual patient 60 to provide for a more reliable and less distorted sound wave reception because of its conforming placement and because its acoustical parameters are more similar to that of a patient's body. As shown, the rigid portion 16 provides a solid support structure for the remaining elements of the device 10.

The diaphragm 21 is preferably flexible and thin, and sealingly covers the sound wave reception aperture 20 of housing structure 15. The diaphragm 21, as shown in FIGS. 2 and 3, has a retainer ring 22 which is a thickened peripheral portion in the diaphragm material itself or which can be a separate mechanical member. The diaphragm 21 is fixed to the housing structure 15 by the cooperation of the retainer ring 22 with the annular groove 23 in the pliant portion 17 of the housing structure 15. Alternatively, the diaphragm 21 can be adhesively secured to the housing structure or the diaphragm can be a thinned area and unitary with the pliant portion 17. It is additionally within the purview of the invention to provide a housing structure 15 comprised of a unitary structure wherein the thickness of the elastomeric material is altered in the housing structure configuration to provide a rigid top area, a semi-rigid lateral area and a flexible bottom membrane area.

In use, the diaphragm 21 is placed in direct contact with the patient body surface 60 (See FIG. 1) to which has been applied the acoustic coupling compound. The flexible diaphragm 21 conforms to the contour of the body surface to vibratingly receive sound waves transmitted from the patient's heart. The vibrations of the diaphragm 21 are transmitted to the hydrophone assembly 26 through the hydrophonic gel 25, which completely fills the inner cavity 24 of the housing structure 15. The hydrophonic gel 25 is a bubble-free, liquid, sound-transmission media such as Aquasonic 100 (T.M.) or Lectro-sonic (T.M.), compounds previously discussed. The air bubble-free media provides for an efficient transmission of acoustic waves so as to minimize acoustic energy losses due to gaseous interference. The fluid ingress-egress aperture 18 in housing structure 15 allows for filling and removal of the hydrophonic gel 25. The aperture 18 is sealable by a screw or plug 19.

Referring to FIG. 3, the hydrophone 26 is centrally placed within the inner cavity 24 of housing structure 15. It produces electrical signals in response to transmitted heart sound waves in the frequency range of 10 to 2,000 Hz. The hydrophone 26 is comprised of a transducer or cantilever crystal beam 27, a current distribution system 30, a hydrophone cavity 61 and an exterior insulating layer 33. The crystal beam 27 is an elongated, thin, and flexible cantilever beam crystal preferably having a length of 3 cm. for receiving acoustic waves through a 10 cm. reception area 20. Contacts 28 are disposed at opposing sides of the crystal beam 27 near its supporting base or mounting end 29. The beam crystal 27 is located within the hydrophone cavity 61 to permit its vibration due to the impact of bioacoustic waves. The beam crystal 27 converts the non-electrical input heart sound waves for example, into an electrical output signal for transmission through cable set 12 via the current distribution system 30.

The crystal 27 is vibratingly sensitive to sound pressure variations and a proportional electric current is produced by its vibration. The current distribution system 30 initiates in and is shielded by hydrophone insulation 33. The current distribution system 30 extends from the contacts 28 of hydrophone 26 and is additionally shielded by an inner insulator 31 and an outer insulator 32 to form a cable 12 which transfers the electrical output current to a heart sound analyzer apparatus 14 or a similar medical diagnostic device, as shown in FIG. 1.

Figure 5:
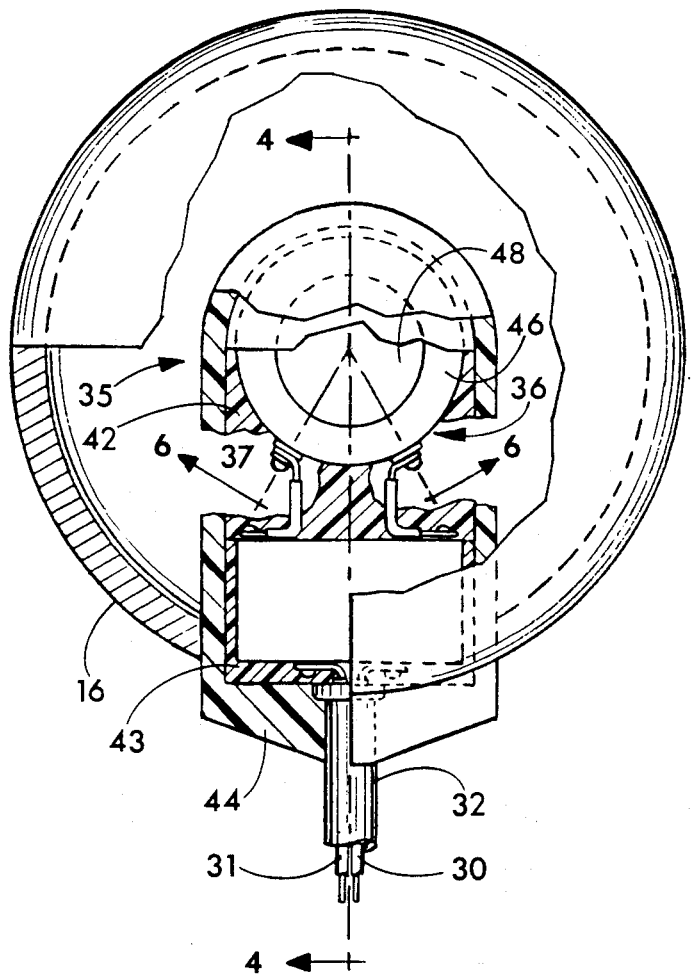
FIG. 5 is a schematic view of the sound sensor device with cut-away portions to further show the hydrophone assembly of FIG. 4.
Figure 4:
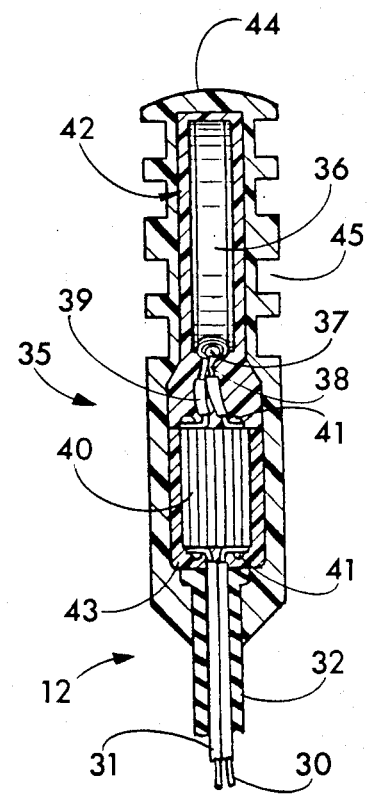
FIG. 4 is a cross-sectional side view taken along lines 4—4 of FIG. 5 showing another embodiment of the hydrophone assembly utilized in the sound sensor of the present invention.

FIGS. 4 and 5 show a alternative hydrophone embodiment 35. Hydrophone 35, as manufactured by Mark Products, Inc. of Houston, Tex., is shown to be comprised of a circular plate transducer 36, transducer insulation 42, a transformer 40, transformer insulation 43, low voltage lead wires 38, lead wires 30 and an exterior hydrophone insulation layer 44. The transducer 36 converts input non-electrical bio-acoustic or heart sound waves into output electrical signal parameters. Variations in the frequency of the output electrical signal parameter being a function of the input parameter. The transducer 36 is further enclosed by a transducer insulator 42, which is composed of a non-conductive substance that does not conduct current or voltage but does conduct sound waves.

Transducer 36 is communicatively connected to a transformer 40 by a pair of low voltage lead wires 38 (approximately 30 gauge). The low voltage lead wires 38 having insulation layer 39 are attached to transducer 36 at transducer contacts 37. Both low voltage lead wires 38 with insulator layers 39 are shown embedded in transducer insulation 42. The transformer 40 is for converting the output electrical signal of the transducer 36 into an electrical signal of the same frequency and increased alternating voltage. The transformer 40 is of a design commonly known in the art. It has a primary and a secondary coil with a magnetic core suitably arranged between them. The output of transducer 36 is received by the primary coil and, by electromagnetic induction, the secondary coil delivers an electrical output signal of an increased voltage. The transformer 40 is enclosed by a transformer insulator 43 which is of a non-conductive material.

As shown, the current distribution system or lead wires 30 are connected to transformer 40 at contacts 41, and they conduct the transformed electrical signal to a heart sound analyzing apparatus 13. Lead wires 30 have a non-conductive inner insulator 31 and a non-conductive outer insulator 32 which collectively form cable set 12.

The hydrophone 35 elements described above and shown in FIG. 4 are further enclosed by an exterior insulation layer 44. The hydrophone insulation 44 protects and electrically insulates the hydrophone elements 40 in the liquid environment of the hydrophonic gel 25. The hydrophone insulation layer 44 is composed of a substance which does not conduct electricity, but does conduct sound waves. As shown particularly in FIG. 4, acoustic channels 45 are formed in the insulation 44. The channels 45 are constructed and arranged in a generally concentric circular configuration on the top and bottom faces of the hydrophone 35 in the areas adjacent to the transducer 36. The channels 45 serve to provide optimal capture of transmitted sound waves. The sound waves are further conducted to the transducer insulator 42 and then to the transducer 36.

Figure 6:
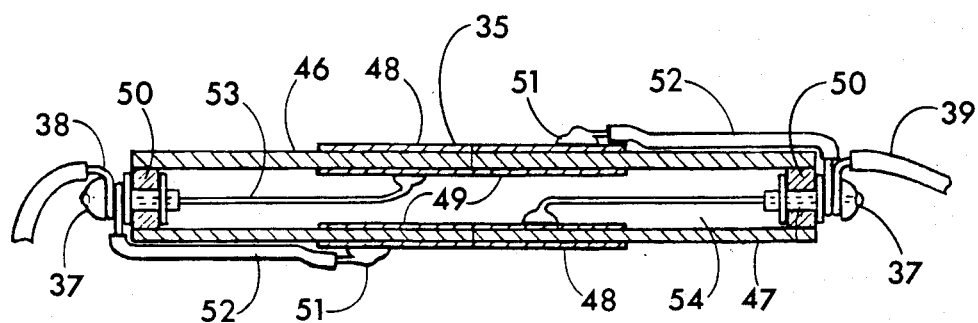
FIG. 6 is a cross-sectional side view taken along lines 6—6 of FIG. 5 and which shows the transducer of the hydrophone assembly.

FIG. 6 shows the circular plate transducer 36 comprising a first plate 46, a second plate 47 and a side wall 50. The first plate 46 and a second plate 47 lie on top of and below the side wall 50 respectively and are bonded thereto. The spacially removed plates 46 and 47 form the transducer void area 54. The first plate 46 and second plate 47 each serve as a base for an outer crystal member 48 and an inner crystal member 49 which are likewise spacially separated in transducer void area 54. The first plate 46, second plate 47 and side wall 50 are composed of a metallic substance suitable for mounting crystals.

The crystal members 48 and 49 are of the type which exhibit the piezoelectric effect. Transmitted sound waves subject the crystal members 48 and 49 to a mechanical stress which sets up an electrical polarization in each crystal and which cause the faces of each crystal to become electrically charged. The polarity of the charges reverses as crystal compression changes to crystal tension. There is an approximately linear relationship between crystal deformation and electric field strength. The change in electric field strength along defined axes in the crystals can be defined by known equations relating to the incremental stress and the piezoelectric strain constant.

The electrical signal produced by crystal members 48 and 49 in response to transmitted sound waves is distributed to the remaining hydrophone 35 conductive elements via outer crystal lead wires 51 and an inner crystal lead wires 53. Each wire 51 and 53 is connected to the transducer contacts 37, to which the low voltage lead wires 38 are also attached. Outer crystal lead wires 51 are substantially sheathed in insulation 52. Inner crystal lead wires 53 are disposed in the transducer void area 54.

Although two embodiments of a hydrophone assembly are here shown and described other such assemblies may also be utilized in the bio-acoustic sound devices of this invention. The criteria being that the hydrophone assembly be mountable in a fluid medium within a housing structure and be designed for receiving and transmitting the bio-acoustic waves and corresponding electrical output signals as discussed above. Once assembled as shown and described, the bio-acoustic sensor of this invention is utilized in various medical diagnostic procedures. Particularly of importance in this invention, as discussed, is the structural arrangement of a heart sound sensor utilizing a hydrophone assembly which cooperates with the other elements of the sensor to detect heart sounds in the sub-KHz range.

In use, the practitioner or researcher selects an area on the thoracic region of the body of a patient for heart sound wave reception and utilizes a medical diagnostic device to analyze heart sound waves. The heart sound sensing device is placed and arranged whereby the diaphragm is in contact with the body surface area of the patient, and the cable means is connected to the medical diagnostic device to accomplish a diagnostic heart sound analysis procedure.

As many changes are possible to the embodiments of this invention utilizing the teachings thereof, the descriptions above, and the accompanying drawings should be interpreted in the illustrative and not the limited sense.

That which is claimed is:

1. A bio-acoustic signal sensing device for placement on the body of a patient to detect low frequency bio-acoustical signals and being for use with medical diagnostic devices, comprising:
   a. a housing structure retaining the remaining elements of the device and having securement means for holding the device to the body of the patient, said housing structure having an open end for sound wave reception and a fluid ingress/egress aperture said open end having a horizontal dimension of at least 5 cm.;
   b. hydrophone means spacially fixed within said housing structure for producing electrical signals in response to transmitted bio-acoustic signals;

c. flexible diaphragm means extended across said open end of said housing structure and having retention means to fix it thereacross, said diaphragm means being for placement in direct contact with the patient body surface, for conforming to the contours of the patient body surface and being vibratingly sensitive to the sound waves generated in the patient's body;

d. a bubble free fluid gel medium filling the remaining interior volume of said housing structure, said fluid medium transmitting sound waves from said diaphragm means to said hydrophone means; and e. cable means communicatively connected to said hydrophone means for transmitting electrical signals from said hydrophone means to medical diagnostic devices.

2. The bio-acoustic signal sensing device of claim 1, wherein said housing structure is further comprised of a rigid top portion and a pliant bottom portion, said rigid top portion having said fluid ingress/egress aperture and having said securement means, said pliant bottom portion defining the open end of said housing structure and having said retention means to fix said diaphragm means at its circumferential periphery, said pliant portion being for conforming to the body curvature of a patient to improve sound wave transmission to said housing structure.

3. A heart sound sensing device for placement on the body of a patient and being for the detection of sub-KHz, low frequency sound waves for use with medical diagnostic devices, comprising:

a. a cylindrical housing structure retaining the remaining elements of the device, said housing structure having a rigid top portion and a pliant bottom portion, said top portion having securement means for holding the device to the body of the patient and a fluid ingress/egress aperture, and said bottom portion having an open end of a diameter of at least 5 cm. for receiving sound waves;

b. hydrophone means centrally fixed within said housing structure for producing electrical signals in response to transmitted sub-KHz frequency heart sound waves, said hydrophone means having a transducer and an exterior insulating covering for converting heart sound waves into electrical output signals;

c. flexible diaphragm means extending across said open end of said pliant bottom portion and having retention means to fix said diaphragm means at the periphery thereof, said diaphragm means being for placement in direct contact with the patient body surface, said diaphragm means and said pliant bottom portion conforming to the contours of the patient body surface and being vibratingly sensitive to sound waves generated by the patient's heart;

d. a bubble free fluid medium completely filling the remaining interior volume of said housing structure about said hydrophone means and surrounding said hydrophone means, said fluid medium transmitting sound waves from said diaphragm means to said hydrophone means; and e. cable means communicatively connected to said hydrophone means for transmitting electrical signals from said hydrophone means to medical diagnostic devices.

4. The sound sensing device of claim 3, wherein said hydrophone means additionally has transformer means for transforming the electrical output signals of said transducer into electrical signals of the same frequency at increased alternating voltages, a transformer insulator, current distribution means for electrical communication between said transducer and said transformer means and thin, resilient insulation covering for said transducer.

5. The sound sensing device of claim 4, wherein said transformer insulator is a rigid non-conductive material to provide strain relief for connection of the sensing device to said cable means.

6. The sound sensing device of claim 3, wherein said transducer is a crystal transducer having two spaced quartz crystal plates producing a piezoelectric effect whereby sound pressure variations cause displacements of the crystals to produce a corresponding voltage.

7. The sound sensing device of claim 6, wherein said hydrophone exterior insulating covering has a plurality of annular channels normal said quartz crystal plated to improve sound wave reception thereto.

8. The sound sensing device of claim 3, wherein said transducer is a cantilever beam crystal transducer having an elongated, thin and flexible crystal at least 3 cm. in length, a base structure to support the cantilevered beam, and two electrical contact points being on opposite sides of said crystal adjacent the base structure for communicating with said cable means of the heart sound sensing device, whereby sound pressure variations cause said flexible crystal to vibrate and produce a corresponding voltage.

9. The sound sensing device of claim 3, wherein said transducer exterior insulating covering is an elastomeric substance which permits the conduction of sound waves.

10. The sound sensing device of claim 3, wherein said diaphragm retention means is comprised of an exteriorly disposed annular groove in said housing structure adjacent its open end and a retention ring to securing said diaphragm means in a taut configuration across said open end.

11. The sound sensing device of claim 10, wherein said diaphragm means is comprised of a circular elastomeric material and wherein said retention ring is comprised of a thickened outer circumferential portion for seating in said housing structure annular groove.

12. The sound sensing device of claim 3, wherein said fluid medium is a phono-transmitting gel.

13. The sound sensing device of claim 3, wherein said housing structure securement means is comprised of at least one exteriorly disposed slotted member and a strap means having connector ends for placement therethrough to adjustably secure said sound sensing device on the body of a patient.

14. A method of sensing heart sound waves comprising:

a. selecting an area on the thoracic region of the body of a patient for heart sound wave reception;

b. providing a medical diagnostic device to analyze heart sound waves;

c. providing a heart sound sensing device having:

(1) a housing structure retaining the remaining elements of said heart sound sensing device and having securement means for holding said device to the body of the patient, said housing structure having an open end for sound wave reception and a fluid ingress/egress port, said open end having a horizontal dimension of at least 5 cm.;

(2) hydrophone means placed within said housing structure for producing electrical signals in response to transmitted heart sound waves;

(3) flexible diaphragm means for placement in direct contact with the patient body surface and which conforms to the contours of the patient body surface and which is vibratingly sensitive to the sound waves generated by the patient's heart, said diaphragm means being extended across said open end of said housing structure and having retention means to fix it thereto;

(4) a bubble free fluid medium transmitting sound waves from said diaphragm means to said hydrophone means, said fluid medium filling the remaining interior volume of said housing structure; and (5) cable means communicatively connected to said hydrophone means for transmission of electrical signals from said hydrophone means to said medical diagnostic device;

d. placing and arranging said heart sound sensing device whereby said diaphragm means is in contact with said body surface area of the patient;

e. connecting said cable means to the medical diagnostic device; and f. performing a diagnostic heart sound analysis procedure.

15. The method of claim 14, wherein an acoustic coupling compound is applied to the selected area of the body of the patient.

16. The method of claim 14, wherein a pair of said sound sensing devices are provided and positioned on the thoracic region of the patient, one said device being placed on the precordial region of the patient adjacent to the sternum and said other device being placed on the high axillary region.

* * * * *